United States Patent
Harju et al.

(10) Patent No.: US 11,590,362 B2
(45) Date of Patent: Feb. 28, 2023

(54) RADIOTHERAPY TREATMENT PLANNING BASED ON TREATMENT DELIVERY EFFICIENCY

(71) Applicant: SIEMENS HEALTHINEERS INTERNATIONAL AG, Palo Alto, CA (US)

(72) Inventors: Ari Harju, Espoo (FI); Juha Kauppinen, Espoo (FI); Esa Kuusela, Espoo (FI)

(73) Assignee: SIEMENS HEALTHINEERS INTERNATIONAL AG

( * ) Notice: Subject to any disclaimer, the term of this patent is extended or adjusted under 35 U.S.C. 154(b) by 90 days.

(21) Appl. No.: 16/830,302

(22) Filed: Mar. 26, 2020

(65) Prior Publication Data
US 2021/0299469 A1 Sep. 30, 2021

(51) Int. Cl.
*A61N 5/10* (2006.01)
(52) U.S. Cl.
CPC ......... *A61N 5/1031* (2013.01); *A61N 5/1047* (2013.01); *A61N 5/1064* (2013.01)
(58) Field of Classification Search
CPC ...... A61N 5/10; A61N 5/1038; A61N 5/1045; A61N 5/1047; A61N 5/1048; A61N 5/1064; A61N 5/1071; A61N 5/1075; A61N 5/1077; A61N 2005/1041; A61N 2005/1072; A61N 5/1031; A61N 5/1001; A61N 5/1039; A61N 2005/1032; A61N 5/1036; A61N 5/1069; A61N 5/103; A61N 5/1042; A61N 5/1043; A61N 2005/1089; A61N 2005/1087; A61N 5/1037; A61N 2005/1074; A61N 5/1081; A61N 5/1049; A61N 2005/1094; A61N 2005/1063; G21K 1/025; G06N 20/00; G16H 30/20;
(Continued)

(56) References Cited

U.S. PATENT DOCUMENTS 8,986,196 B2 * 3/2015 Larkin ................... A61B 34/30
606/1
9,381,376 B2 * 7/2016 Toimela ............... A61N 5/1064
(Continued)

OTHER PUBLICATIONS

Byron Wilson et al., "Sci-Thur AM: YIS—09: Treatment Time Optimization for Trajectory-Based Deliveries", Medical Physics—Sixty-second annual scientific meeting of the Canadian organization of medical physicists, Aug. 2, 2016, vol. 43, Issue 8 Part 3.

*Primary Examiner* — Irakli Kiknadze
(74) *Attorney, Agent, or Firm* — Su IP Consulting

(57) ABSTRACT

Example methods and systems for radiotherapy treatment planning based on treatment delivery efficiency are described. One example method may comprise a computer system configuring dosimetric planning objective(s) and non-dosimetric planning objective(s) associated with efficiency of treatment delivery. A set of multiple treatment plan variants may be generated based on the dosimetric planning objective(s) and non-dosimetric planning objective(s). A first treatment plan associated with a first tradeoff and a second treatment plan associated with a second tradeoff may then be identified from the set of multiple treatment plan variants. The second treatment plan may be associated with improved efficiency of treatment delivery compared to the first treatment plan.

21 Claims, 10 Drawing Sheets

(58) Field of Classification Search
CPC ........ G16H 50/20; G16H 20/40; G16H 50/50; G16H 30/40
USPC .......................................................... 378/65
See application file for complete search history.

(56) References Cited

U.S. PATENT DOCUMENTS

| | | | |
|---|---|---|---|
| 9,987,504 B2 * | 6/2018 | Nord | A61N 5/103 |
| 10,213,621 B2 * | 2/2019 | Bush | A61N 5/1081 |
| 10,850,126 B2 * | 12/2020 | Binnekamp | A61B 5/065 |
| 2003/0086529 A1 * | 5/2003 | Clark | A61B 6/467 |
| | | | 378/65 |
| 2003/0095625 A1 * | 5/2003 | Steinberg | A61N 5/1048 |
| | | | 378/65 |
| 2012/0136194 A1 * | 5/2012 | Zhang | A61N 5/103 |
| | | | 600/1 |
| 2015/0367144 A1 * | 12/2015 | Flynn | A61N 5/1039 |
| | | | 600/7 |
| 2017/0189715 A1 * | 7/2017 | Isola | A61N 5/1031 |
| 2018/0280725 A1 * | 10/2018 | Sheng | A61N 5/1047 |

\* cited by examiner

RADIOTHERAPY TREATMENT PLANNING BASED ON TREATMENT DELIVERY EFFICIENCY

BACKGROUND

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the objective is to deliver a lethal or curative radiation dose to the tumor, while maintaining an acceptable dose level in the proximal healthy structures. However, in practice, there are various challenges associated with radiotherapy treatment planning to achieve this objective. In some cases, clinicians may have other planning objectives that are not considered in conventional radiotherapy treatment planning.

SUMMARY

According to examples of the present disclosure, methods and systems for radiotherapy treatment planning based on treatment delivery efficiency are described. One example may comprise a computer system configuring dosimetric planning objective(s) and non-dosimetric planning objective(s) associated with efficiency of treatment delivery. A set of multiple treatment plan variants may be generated based on the dosimetric planning objective(s) and non-dosimetric planning objective(s). From the set of multiple treatment plan variants, a first treatment plan associated with a first tradeoff and a second treatment plan associated with a second tradeoff may be identified. The second treatment plan may be associated with improved efficiency of treatment delivery compared to the first treatment plan.

DETAILED DESCRIPTION

Figure 1:
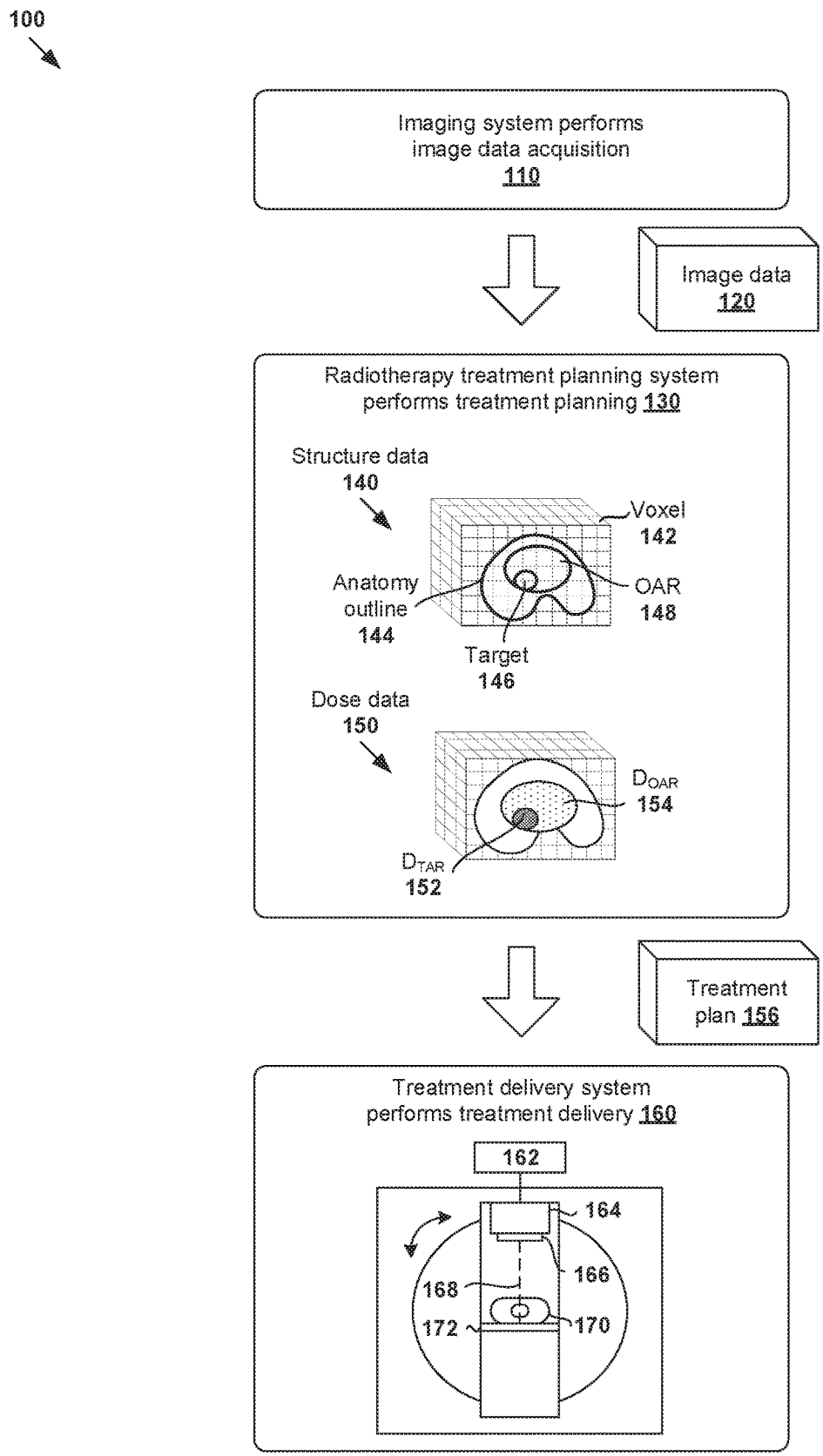
FIG. 1 is a schematic diagram illustrating an example process flow for radiotherapy treatment based on treatment delivery efficiency.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated herein.

FIG. 1 is a schematic diagram illustrating example process flow 100 for radiotherapy treatment. Example process flow 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), magnetic resonance tomography (MRT), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures from image data 120. In practice, a three-dimensional (3D) volume of the patient's anatomy may be reconstructed from image data 120.

The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may include any suitable data relating to the contour, shape, size and location of patient's anatomy 144, target 146, organ-at-risk (OAR) 148, or any other structure of interest (e.g., tissue, bone). For example, using image segmentation, a line may be drawn around a section of an image and labeled as target 146 (e.g., tagged with label="prostate"). Everything inside the line would be deemed as target 146, while everything outside would not.

In another example, dose prediction may be performed to generate dose data 150 specifying radiation dose to be delivered to target 146 (denoted "DTAR" at 152) and radiation dose for OAR 148 (denoted "DoAR" at 154). In practice, target 146 may represent a malignant tumor (e.g., prostate tumor) requiring radiotherapy treatment, and OAR 148 a proximal healthy structure or non-target structure (e.g., rectum, bladder) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated to include 2D fluence map data for a set of beam orientations or angles. Each fluence map specifies the intensity and shape (e.g., as determined by a multi-leaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system. In practice, block 130 may be performed based on goal doses prescribed by a clinician (e.g., oncologist, dosimetrist, or planner), such as based on the clinician's experience, the type and extent of the tumor, patient geometry and condition.

At 160 in FIG. 1, treatment delivery is performed during a treatment phase to deliver radiation to the patient according to treatment plan 156. For example, radiotherapy treatment delivery system 160 ("treatment machine") may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, brachy therapy, sirex spheres, any combination thereof, etc. Additionally, examples of the present disclosure may be applicable to particle delivery systems (e.g., proton, carbon ion). Such systems may employ either a scattered particle beam that is then shaped by a device akin to an MLC, or a scanning beam of adjustable energy, spot size and dwell time. Also, OAR segmentation might be performed, and automated segmentation of the applicators might be desirable.

Figure 2:
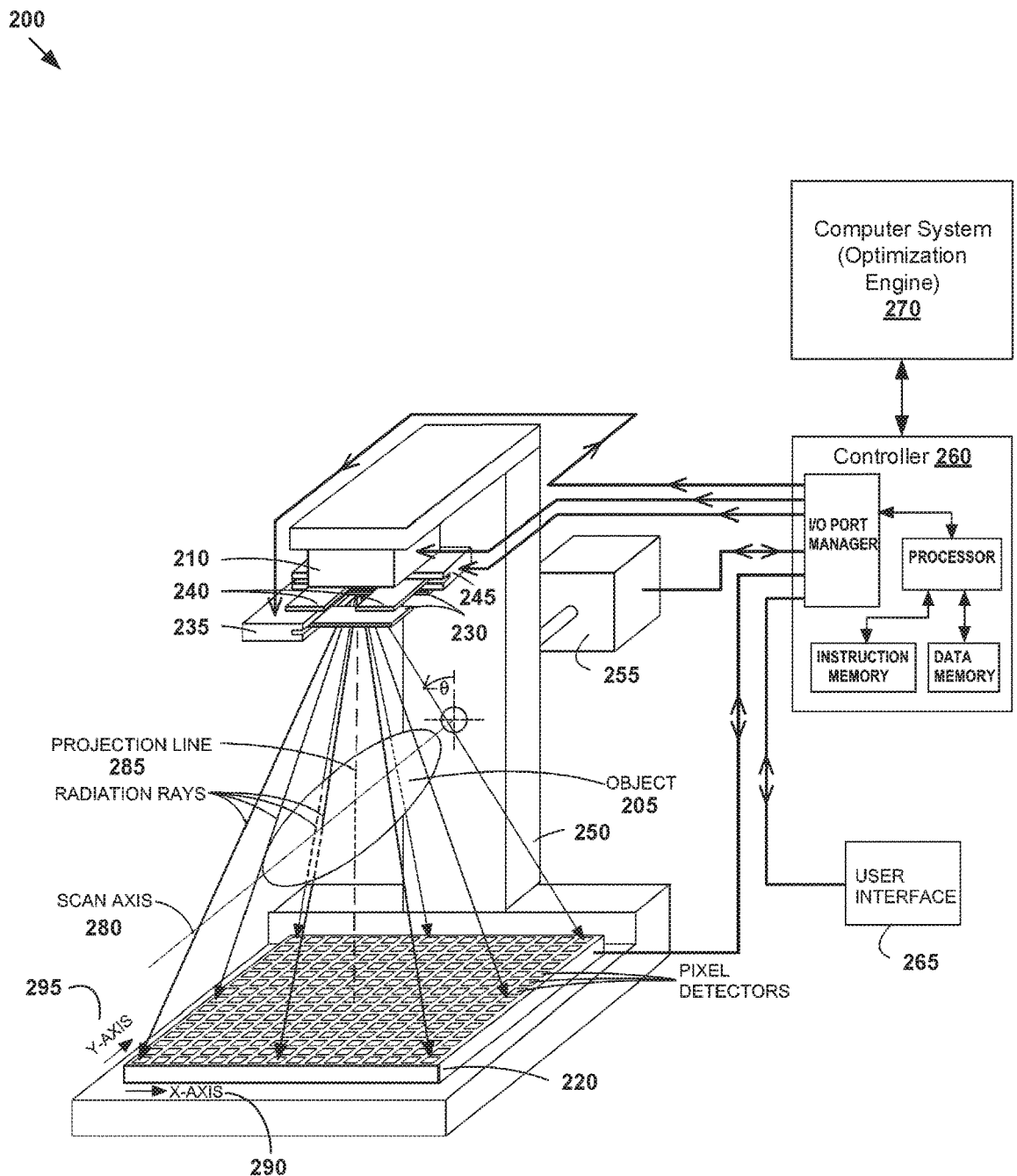
FIG. 2 is a schematic diagram illustrating an example imaging system.

FIG. 2 is a schematic diagram illustrating example imaging system 200. Although one example is shown, imaging system 200 may have alternative or additional components depending on the desired implementation in practice. In the example FIG. 2, imaging system 200 includes radiation source 210; detector 220 having pixel detectors disposed opposite to radiation source 210 along a projection line (defined below; see 285); first set of fan-beam blocking blades 230 disposed between radiation source 210 and detector 220; and first fan-beam blocking blade drive 235 to hold fan-beam blocking blades 230 and set their positions.

Imaging system 200 may further include second set of fan-beam blocking blades 240 disposed between radiation source 210 and detector 220, and second fan-beam blocking blade drive 245 that holds fan-beam blocking blades 240 and sets their positions. The edges of fan-beam blocking blades 230-240 may be oriented substantially perpendicular to scan axis 280 and substantially parallel with a trans-axial dimension of detector 220. Fan-beam blocking blades 230-240 are generally disposed closer to the radiation source 210 than detector 220. They may be kept wide open to enable the full extent of detector 220 to be exposed to radiation but may be partially closed in certain situations.

Imaging system 200 may further include gantry 250 that holds at least radiation source 210, detector 220, and fan-beam blocking blade drives 235 and 245 in fixed or known spatial relationships to one another, mechanical drive 255 that rotates gantry 250 about target object 205 disposed between radiation source 210 and detector 220, with target object 205 being disposed between fan-beam blocking blades 230 and 240 on the one hand, and detector 220 on the other hand. The term "gantry" may cover all configurations of one or more structural members that can hold the above-identified components in fixed or known (but possibly movable) spatial relationships. For the sake of visual simplicity in the figure, the gantry housing, gantry support, and fan-blade support are not shown.

Additionally, imaging system 200 may include controller 260, user interface 265, and computer system 270. Controller 260 may be electrically coupled to radiation source 210, mechanical drive 255, fan-beam blocking blade drives 235 and 245, detector 220, and user interface 265. User interface 265 may be configured to enable a user to at least initiate a scan of target object 205, and to collect measured projection data from detector 220. User interface 265 may be configured to present graphic representations of the measured projection data. Computer system 270 may be configured to perform any suitable operations, such as tomographic image reconstruction and analysis according to examples of the present disclosure.

Gantry 250 may be configured to rotate about target object 205 during a scan such that radiation source 210, fan-beam blocking blades 230 and 240, fan-beam blocking blade drives 235 and 245, and detector 220 circle around target object 205. More specifically, gantry 250 may rotate these components about scan axis 280. As shown in FIG. 2, scan axis 280 intersects with projection lines 285, and is typically perpendicular to projection line 285. Target object 205 is generally aligned in a substantially fixed relationship to scan axis 280. The construction provides a relative rotation between projection line 285 on one hand, and scan axis 280 and target object 205 aligned thereto on the other hand, with the relative rotation being measured by an angular displacement value θ.

Mechanical drive 255 may be coupled to the gantry 250 to provide rotation upon command by controller 260. The array of pixel detectors on detector 220 may be periodically read to acquire the data of the radiographic projections (also referred to as "measured projection data" below). Detector 220 has X-axis 290 and Y-axis 295, which are perpendicular to each other. X-axis 290 is perpendicular to a plane defined by scan axis 280 and projection line 285, and Y-axis 295 is parallel to this same plane. Each pixel on detector 220 is assigned a discrete coordinate along X-axis 290 and Y-axis 295. A smaller number of pixels are shown in the figure for the sake of visual clarity. Detector 220 may be centered on projection line 285 to enable full-fan imaging of target object 205, offset from projection line 285 to enable half-fan imaging of target object 205, or movable with respect to projection line 285 to allow both full-fan and half-fan imaging of target object 205.

During radiotherapy treatment planning at block 130 in FIG. 1, treatment plan 156 may be designed to deliver radiation as prescribed by a radiation oncologist with the intention of curing, reducing the recurrence risk of, or providing palliative relief from cancer. Conventionally, treatment planning objectives are generally dosimetric in nature to deliver the prescribed dose to target 146 while minimizing dose absorbed by OAR(s) 148. However, the consideration of dosimetric objectives (e.g., delivered dose distribution) alone may lead to undesirable planning outcomes. In one example, complicated treatment plans that have complex field geometry and/or require more modulation may increase treatment duration.

Treatment Delivery Efficiency

According to examples of the present disclosure, radiotherapy treatment planning may be improved according to an "efficiency-aware" approach. In particular, during radiotherapy treatment planning, a treatment plan may be generated by considering dosimetric planning objective(s) together with non-dosimetric planning objective(s) associated with treatment delivery efficiency. Here, the term "efficiency" or "treatment delivery efficiency" may refer generally to a measure of the amount of resource(s) required to deliver a treatment plan using a treatment machine. For example, a treatment delivery resource may be treatment duration (e.g., length of treatment time at a clinic), physical resource, treatment machine parameter, etc. Examples of the present disclosure may be implemented to reduce the likelihood of generating treatment plans having good quality metrics but are inefficient to deliver.

Figure 3:
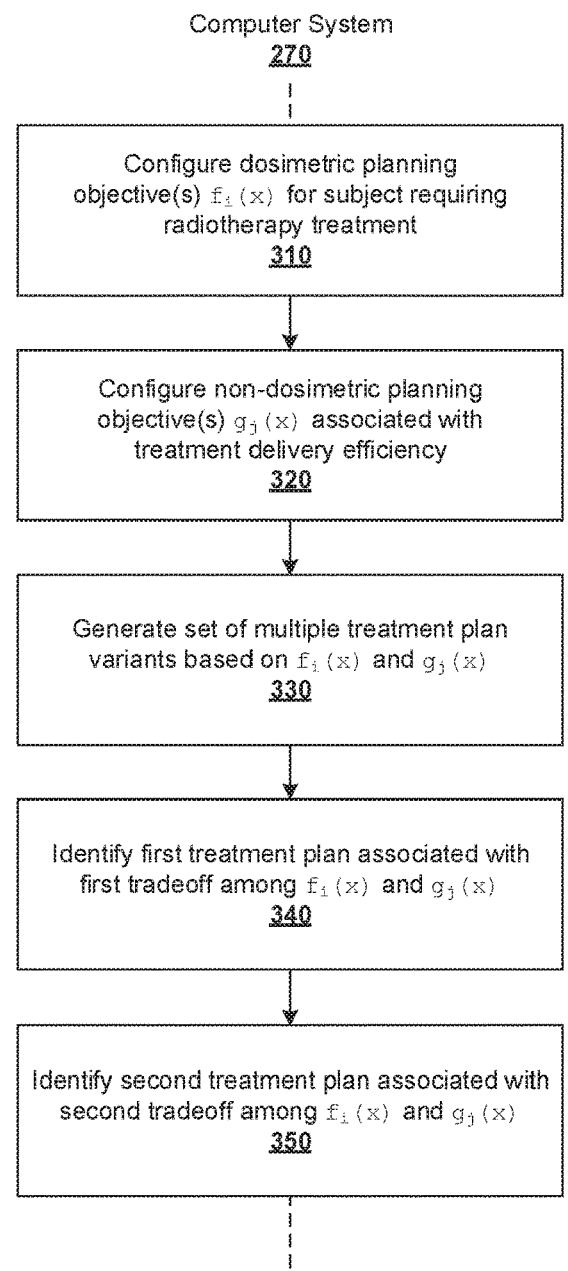
FIG. 3 is a flowchart of an example process for a computer system to perform radiotherapy treatment planning based on treatment delivery efficiency.

In more detail, FIG. 3 is a flowchart of example process 300 for a computer system to perform radiotherapy treatment planning based on treatment delivery efficiency. Example process 300 may include one or more operations, functions, or actions illustrated by one or more blocks, such as 310 to 350. The various blocks may be combined into fewer blocks, divided into additional blocks, and/or eliminated based upon the desired implementation. Example process 300 may be implemented using any suitable computer system(s), such as computer system 270 supporting an optimization engine in FIG. 2. An example computer system will also be discussed using FIG. 8.

At 310 in FIG. 3, dosimetric planning objective(s) for a subject requiring radiotherapy treatment may be configured. At 320, non-dosimetric planning objective(s) associated with efficiency of treatment delivery to the subject using a treatment machine may be configured. At 330, a set of multiple treatment plan variants may be generated based on dosimetric planning objective(s) and non-dosimetric planning objective(s). Depending on the desired implementation, the dosimetric and non-dosimetric planning objective(s) may be configured based on input data from a user (e.g., clinician). Any suitable treatment machine may be used, such as VMAT-based system, IMRT-based system, etc.

As will be discussed further using FIG. 4 and FIG. 5, a non-dosimetric planning objective may be configured based on treatment delivery duration, monitor unit (MU), IMRT fluence smoothing level, IMRT adjacent leaf synchronization level, IMRT or VMAT dose rate modulation level, VMAT leaf modulation level, primary fluence mode, number of treatment fields, number of isocenter positions, allowed range for a machine axis, maximum machine axis speed and type of MLC technique (e.g., VMAT, IMRT). In practice, the non-dosimetric planning objective(s) may be configured at block 320 to reduce consumption of treatment delivery resource(s), such as by reducing the complexity of treatment plan and associated treatment duration.

At 340 in FIG. 3, a first treatment plan may be identified from the set of multiple treatment plan variants. At 350, a second treatment plan may be identified from the set of multiple treatment plan variants. The first treatment plan may be associated with a first tradeoff among the dosimetric planning objective(s) and non-dosimetric planning objective(s). The second treatment plan may be associated with a second tradeoff that varies from the first tradeoff, and improved efficiency of treatment delivery compared to the first treatment plan.

Examples of the present disclosure should be contrasted against conventional approaches that only consider dosimetric properties during radiotherapy treatment planning. Without the consideration for treatment delivery efficiency, factors such as how complicated a treatment plan is or how much modulation is used to achieve a certain dose distribution may be neglected. Further, if treatment is optimized using a dose rate that is two times higher than in the actual treatment machine, the real treatment duration is doubled. By improving treatment delivery efficiency, treatment time slots at clinics may be better utilized to improve clearance, while facilitating better management between demanding and substantially easy cases. Various examples will be discussed below.

Planning Objective Configuration

Figure 4:
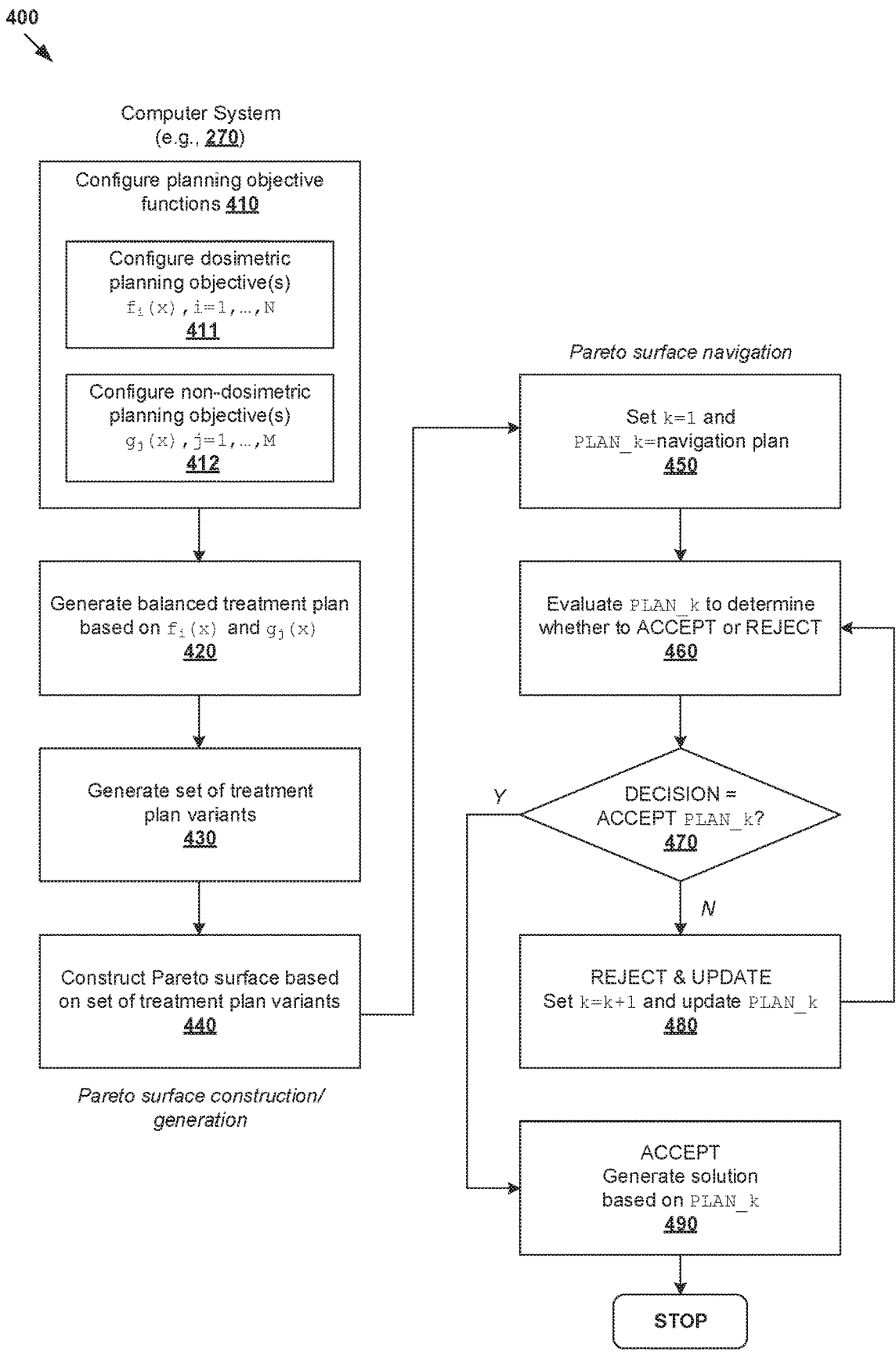
FIG. 4 is a flowchart of an example detailed process for a computer system to perform radiotherapy treatment planning based on treatment delivery efficiency.

FIG. 4 is a flowchart of example process 400 for a computer system to perform radiotherapy treatment planning based on treatment delivery efficiency. Example process 400 may include one or more operations, functions, or actions illustrated by one or more blocks, such as 410 to 480. The various blocks may be combined into fewer blocks, divided into additional blocks, and/or eliminated based upon the desired implementation. Example process 400 may be implemented using any suitable computer system(s), an example of which will be discussed using FIG. 8.

At 410 in FIG. 4, a radiotherapy treatment planning may be formulated as a multi-criteria optimization (MCO) problem using a combination of dosimetric and non-dosimetric objective functions. Given x=treatment plan, X=set of all feasible treatment plans, $\{f_i(x)\}$=set of dosimetric objective function(s) and $\{g_j(x)\}$=set of non-dosimetric objective function(s) associated with treatment plan delivery, the MCO problem may be defined as follows:

minimize $\{f_i(x), g_j(x)\}$ subject to x∈χ, $f_i(x) \leq 0$, for i=1, . . . , N and N≥1, and $g_j(x) \leq 0$, for j=1, . . . , M and M≥1.

In a Pareto sense, a feasible $x^* \in \chi$ is referred to as "Pareto optimal" if there is no feasible x such that $f_i(x) \leq f_i(x^*)$ and $g_j(x) \leq g_j(x^*)$ for the set of objective functions, with a strict inequality for at least one objective function. The optimization process may be guided by any suitable constraint(s) configured for each objective function. The set of Pareto-optimal solutions is referred to as the "Pareto frontier" or "Pareto surface." In practice, there might be an infinite number of Pareto-optimal solutions in the solution space $\chi$. During radiotherapy treatment planning, a treatment plan may be selected from the Pareto frontier, which may be a subjective decision depending on preferences of a treatment planner.

At 411 in FIG. 4, a first set of N≥1 dosimetric objective function(s) may be configured. Each $f_i(x)$, where i=1, . . . , N, may be configured to achieve a dosimetric quality metric. In practice, $f_i(x)$ may be associated with any suitable patient's structure(s), such as target volume, OAR or proximal healthy structure volume, relative overlap volume (i.e., fraction of target volume overlapping with OAR volume), relative out-of-field volume (i.e., fraction of target or OAR volume outside of the treatment field), etc. Objective function $f_i(x)$ may be expressed in terms of mean dose, median dose, 3D dose distribution, 2D dose-volume histograms (DVH), etc. In general, a 3D dose distribution defines the magnitude of radiation at each 3D voxel representing a target or OAR. 3D dose distributions may be summarized using DVH in a 2D format.

In relation to prostate cancer, one example $f_i(x)$ may be associated with a desired dose distribution for target=prostate and another for OAR(s)=rectum or bladder. For lung cancer, $f_i(x)$ may specify a desired dose distribution for target=cancerous lung tissue, or OAR(s)=proximal healthy lung tissue, esophagus or heart. For brain cancer, $f_i(x)$ may specify a desired dose distribution for target=brain tumor, or OAR(s)=proximal optic nerve or brain stem. In another example, $f_i(x)$ may define a planning objective for target homogeneity, such as based on a homogeneity index (h-index) representing a ratio of the maximum dose in the target volume to a corresponding prescribed dose. Radiation dose may be measured in Gray (Gy), which represents the absorption of one joule of radiation energy in one kilogram of matter.

At 412 in FIG. 4, a second set of M≥1 non-dosimetric objective function(s) may be configured. Each $g_j(x)$, where j=1, . . . , M, may be configured to achieve a quality metric relating to treatment delivery by system 160 (see FIG. 1). Depending on the desired implementation, $g_j(x)$ may be treatment duration objective, MU objective, machine parameter objective, etc. Some examples are discussed below.

(a) Treatment duration objective(s) may be configured to achieve a better balance between dosimetric gain and the penalty of increased treatment duration. This way, the treatment duration of different patients may be adjusted to achieve a better balance between demanding and easy cases. By considering treatment duration as one of the objectives in the MCO problem, examples of the present disclosure may be implemented to improve clearance at clinics and adjust treatment time slots to deliver better treatment for more patients.

(b) MU objective(s) may be configured to optimize the MU count of a treatment delivery system while achieving clinically acceptable dosimetric quality metric(s). In practice, MU is a measure of machine output from a clinical accelerator for radiotherapy, such as a linear accelerator or an orthovoltage unit. A single MU may represent the amount of charge recorded in the ionization chamber mounted in the head of the linear accelerator, which correlates to one centigray (cGy) of absorbed dose in water under some reference conditions. In practice, a reduced MU count may indicate that less radiation energy is lost due to irradiation through small apertures. Increase in lost radiation energy also indicates more unwanted radiation scatter from a treatment machine.

(c) Machine parameter objective(s) may be expressed as a function of IMRT-related parameter(s), VMAT-related parameter(s), etc. Examples include IMRT fluence smoothing level, IMRT adjacent leaf synchronization level (e.g., defined by the American Society of Clinical Oncology (ASCO)), IMRT dose rate modulation level, VMAT leaf modulation level (also controlled by ASCO), VMAT dose rate modulation level, primary fluence mode, number of treatment fields, number of treatment isocenter positions, allowed range for a machine axis (e.g., axis for gantry angle, couch angle, leaf position), maximum machine axis speed (e.g., axis for leaf speed, gantry angle, dose rate), choice of MLC technique (e.g., VMAT, IMRT), etc.

Using IMRT, a set of photon beams with modulated fluences (i.e., time-accumulated intensities) to deliver treatment. An accelerator gantry may be rotated to irradiate a patient from different angles, and metal leaves on an MLC shape the profiles of the radiation fields. Example delivery techniques may include segmented MLC (SMLC) and dynamic MLC (DMLC). In both cases, the total dose delivered is determined by the superposition of the radiation fields of all beams. Unlike IMRT, which generally includes a number of (e.g., ten) fixed-field beam angles, VMAT includes a larger number of beam directions from an arc trajectory. This way, doses may be delivered dynamically during irradiation by rotating the gantry continuously. From each beam direction, modulation is not performed such that the intensity is uniform.

In practice, tradeoffs among dosimetric and non-dosimetric objective functions may be configured by assigning a weight to each objective function to represent its relative importance. For example, weight $w_i$ may be assigned to the $i^{th}$ dosimetric objective function $f_i(x)$ and weight $w_{N+j}$ to the $j^{th}$ non-dosimetric objective function $g_j(x)$. A treatment planner may adjust the relative importance or priority of each objective function depending on any suitable factors. For example, a "balanced plan" may be generated by setting equal weight for each objective function. From the balanced plan, a set of treatment plan variants may be generated by adjusting the weight of at least one objective function to increase or decrease its relative importance compared to the balanced plan.

Pareto Surface Generation

Blocks 420-440 in FIG. 4 will be explained using FIG. 5, which is a schematic diagram illustrating example Pareto surface generation 500 for radiotherapy treatment planning based on treatment delivery efficiency. In the following, consider an example radiotherapy treatment planning for prostate cancer treatment based on patient data 510, which may include medical image data 511 acquired using imaging system 200 in FIG. 2. Image data 511 may include 2D or 3D images of any suitable anatomical site(s) of a patient's anatomy. The anatomical site may be generic for medical image data, or specific to a particular treatment. Structure data 512 may identify any suitable contour, shape, size and/or location of structure(s) identifiable from image data 511. Example structures may include target(s), OAR(s) or any other structure of interest (e.g., tissue, bone). Structure data 512 may be generated by performing automatic and/or manual segmentation on image data 511.

To identify a treatment plan for the patient, consider the case of N=2 dosimetric objectives and M=1 non-dosimetric objective for prostate cancer treatment planning. For example, $f_1(x)$ and $f_2(x)$ (see 521-522) may be configured to achieve target homogeneity and dose conformity for a target volume (e.g., substantially high dose to target=rectum), respectively. Non-dosimetric objective function $g_1(x)$ may specify a treatment duration objective (see 523) for a treatment delivery system, such as an IMRT-based or VMAT-based treatment delivery system.

Figure 5:
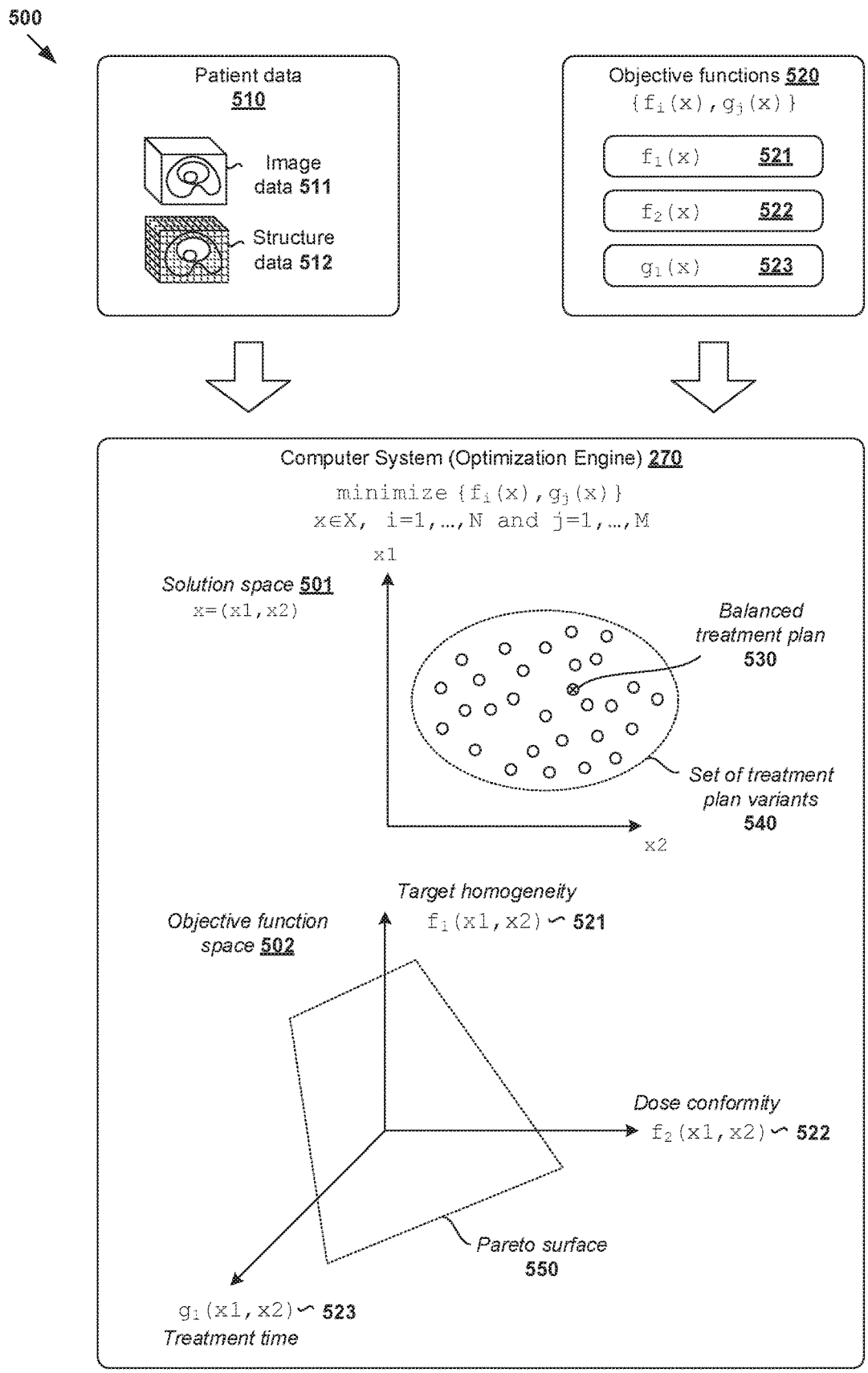
FIG. 5 is a schematic diagram illustrating an example Pareto surface generation for radiotherapy treatment planning based on treatment delivery efficiency.

In practice, treatment plan x in may be presented as a multi-dimensional vector in a solution space (see 501), such as 2D vector x=(x1, x2) where x1 and x2 are two parameters related to the treatment plan generation process, such as two objective locations in dose optimization (see FIG. 5). A "treatment plan" may include any suitable data and/or instructions processible by a treatment machine to deliver radiotherapy treatment. For example, a treatment plan may include parameters such as the number of beams, their incident angles and gantry speed.

At 420 and 430 in FIG. 4, an initial treatment plan and a set of treatment plan variants may be generated based on objective functions $f_i(x)$ and $g_j(x)$. In the example in FIG. 5, initial treatment plan 530 may be a balanced plan that is generated by assigning an equal weight w=1/(N+M) to each objective function. In other words, the balanced plan is generated based on an equal tradeoff among dosimetric and non-dosimetric objectives is considered. Based on balanced treatment plan 530, a set of multiple treatment plan variants (see 540) may be generated, such as by adjusting weights ($w_1$, $w_2$, $w_3$) assigned to respective $f_1(x)$, $f_2(x)$ and $g_1(x)$ such that each quality metric value gets more (or less) emphasis compared to balanced treatment plan 530.

Treatment plan variants 540 may represent a set of Pareto-optimal treatment plans that are each associated with a different tradeoff among objective functions $f_i(x)$ and $g_j(x)$. Depending on the desired implementation, block 430 may involve excluding treatment plan(s) having inferior dosimetric metrics (e.g., inferior clinical outcome) according to $f_i(x)$ and inferior treatment delivery efficiency (e.g., longer treatment duration) from set 540. This way, such inferior plans may be excluded from subsequent Pareto surface navigation below. Treatment plan variants 540 may be generated using any suitable approach, such as using template(s) to facilitate automatic treatment plan generation according to the desired variations.

For IMRT-based treatment plan optimization, treatment plan variants 540 with different treatment durations may be generated using different fluence smoothing parameters, or similar parameters that control the modulation in the optimal fluence. In one example, treatment plan variants 540 may be generated using different fluence smoothing parameters. Higher fluence smoothing parameter(s) may be configured to generate treatment plan variants with shorter treatment duration. Depending on the desired implementation, direct fluence smoothing may be replaced by a more detailed objective term to better control the treatment duration, for example direct IMRT sliding window leaf motion optimization may result in a leaf sequence which can be delivered faster. Some choices affecting the treatment duration (e.g., number of arcs in VMAT) may be discrete and generally quite difficult to optimize together with the continuous degrees-of-freedom relating to dosimetric properties.

For VMAT-based treatment plan optimization, external photon treatment plans of different treatment durations may be generated by unphysical scaling of the three machine speed limits of dose, gantry and collimator leaves. The treatment duration may be obtained using one of these velocities. In this case, block 430 may involve scaling all (real machine) speed limits with a constant value to generate treatment plan variants 540. In general, a particular treatment plan variant is a non-continuous function of the speed limits, and in a normal case, a topologically different solution is obtained. The transformation between solution is generally highly non-conformal, and any scaling argument may fail for any scaling parameter of the velocities that is far from unity. The optimization process may be repeated for different speed limits.

At 440 in FIG. 4, a Pareto surface (see 550 in FIG. 5) may be constructed based on treatment plan variants 540. For example, based on objective functions $f_1(x)$, $f_2(x)$ and $g_1(x)$, Pareto surface 550 may be a piecewise, linear hyperplane going through all the points associated with set of treatment plan variants 540. Each treatment plan solution (x) in decision variable space 501 may correspond with a point on Pareto surface 540 in a multi-dimensional objective space 502.

Once the set of Pareto-optimal treatment plans has been obtained, the set may be "navigated" according to blocks 450-490 to find a solution considering the tradeoffs among different objective functions. This optimization process is also known as Pareto surface navigation. The Pareto surface may be generated as a space having one dimension for each quality metric specified by an objective function. The Pareto surface may be defined as a piecewise linear hyperplane (with one dimension less) going through all the points on a hyperspace defined by treatment plan variants. As will be described below, a navigation step during the optimization process may involve a planner expressing their subjective preferences among the tradeoffs.

Pareto Surface Navigation

To select a single Pareto-optimal solution from the solution space X, various iterations of Pareto surface navigation may be performed until a treatment plan of suitable quality is found. Pareto surface 550 in FIG. 5 may be navigated through interpolation of treatment plan variants 540. Each navigation step amounts to setting a preference among different tradeoffs, as expressed using weights assigned to different objective functions $f_1(x)$, $f_2(x)$ and $g_1(x)$. As such, in addition to dosimetric considerations, the solution space may be augmented by metric(s) relating to how efficiently a treatment plan can be delivered.

Referring to FIG. 4 again, at 450, a navigation plan may be selected from set of treatment plan variants 540. The navigation plan (denoted as PLAN_k) represents a treatment plan that will be evaluated at a particular navigation step k. At 460 and 470, an evaluation of the navigation plan (PLAN_k) may be performed to determine whether to accept or reject the navigation plan. At 480, in response to determination to reject the navigation plan, an updated navigation plan may be generated for the next navigation step (i.e., k=k+1), such as by adjusting metric(s) associated with PLAN_k.

In practice, block 480 in FIG. 4 may be performed based on input from a user (e.g., clinician). For example, if the user defines a desired improvement associated with target homogeneity according to $f_1(x)$, computer system 270 may determine an optimal way to degrade other objectives as little as possible. Similarly, if the user defines a desired improvement in treatment duration according to $g_1(x)$, computer system 270 may determine how plan quality reduction might be shared between dosimetric objectives according to $f_1(x)$ and $f_2(x)$.

Figure 6:
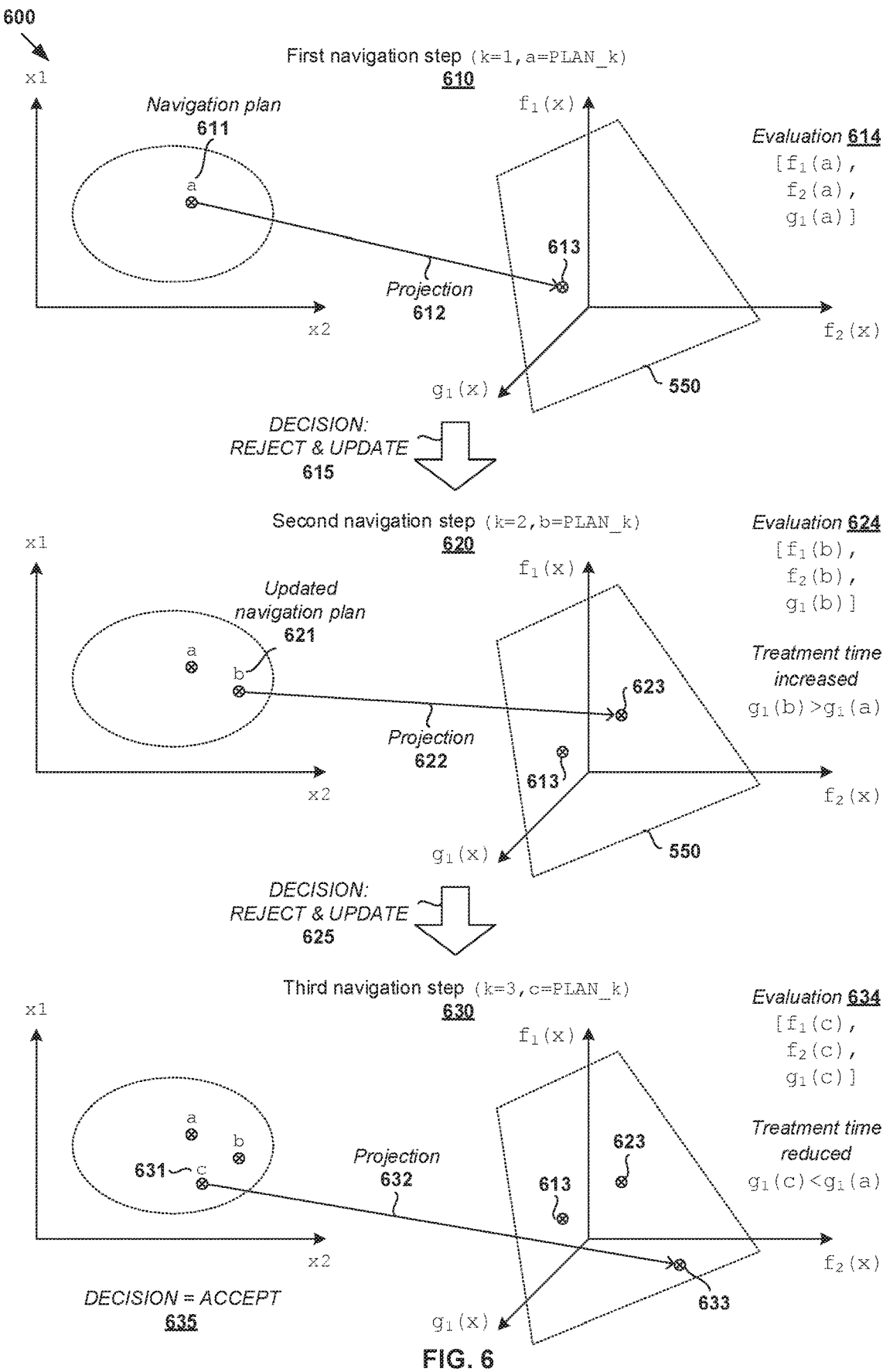
FIG. 6 is a schematic diagram illustrating an example Pareto surface navigation for radiotherapy treatment planning based on treatment delivery efficiency.

Blocks 460, 470 and 480 may be repeated until a treatment plan of suitable quality and treatment delivery efficiency is identified and accepted at block 490. Some example navigation steps will be explained using FIG. 6, which is a schematic diagram illustrating example Pareto surface navigation 600 for radiotherapy treatment planning based on treatment delivery efficiency. At 610 (k=1), a first navigation step may involve computer system 270 configuring balanced treatment plan 530 to be a first navigation plan 611 denoted as PLAN_k=a for k=1. A corresponding point (see 613) in objective space 502 may be identified through projection 612 onto Pareto surface 550. Based on an evaluation (see 614) of PLAN_k=a according to $f_1(a)$, $f_2(a)$ and $g_1(a)$, the current navigation plan may be accepted or rejected (see 615).

At 620 (k=2), a second navigation step may involve generating updated navigation plan 621 denoted as $PLAN_k$=b for k=2 based on first navigation plan 611. A corresponding point (see 623) in objective space 502 may be identified through projection 622 onto Pareto surface 550. Based on an evaluation (see 624) of $PLAN_k$=b according to $f_1(b)$, $f_2(b)$ and $g_1(b)$, updated navigation plan 621 may be accepted or rejected. For example, updated navigation plan 621 may be associated with improved dosimetric quality but longer treatment duration compared to first navigation plan 611. Based on evaluation 624, a REJECT decision may be made (see 625) to search for another treatment plan having a shorter treatment duration.

At 630 (k=3), a third navigation step may involve generating updated navigation plan 621 denoted as $PLAN_k$=c for k=3 based on second navigation plan 621. A corresponding point (see 633) in objective space 502 may be identified through projection 632 onto Pareto surface 550. Next (see 634), $PLAN_k$=b may be evaluated according to $f_1(b)$, $f_2(b)$ and $g_1(b)$. In the example in FIG. 6, updated navigation plan 631 may be associated with improved dosimetric quality but shorter treatment duration compared to first navigation plan 611 and second navigation plan 612. Once the desired quality is achieved, an ACCEPT decision may be made (see 635). During treatment delivery, a treatment plan that reflects the quality of $PLAN_k$=c may be delivered to the patient.

Figure 7A:
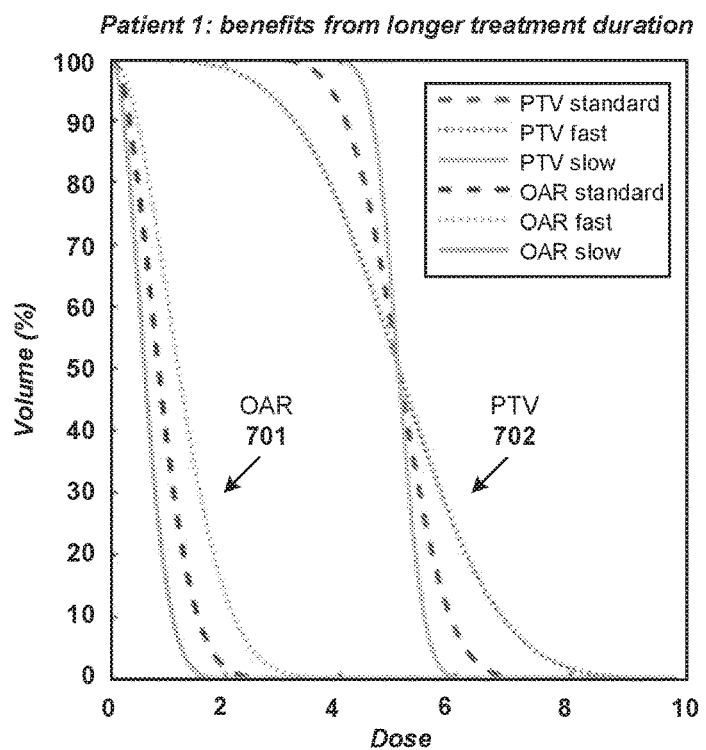
FIG. 7A is a graph illustrating example dose volume histograms (DVH) curves associated with a first patient case.
Figure 7B:
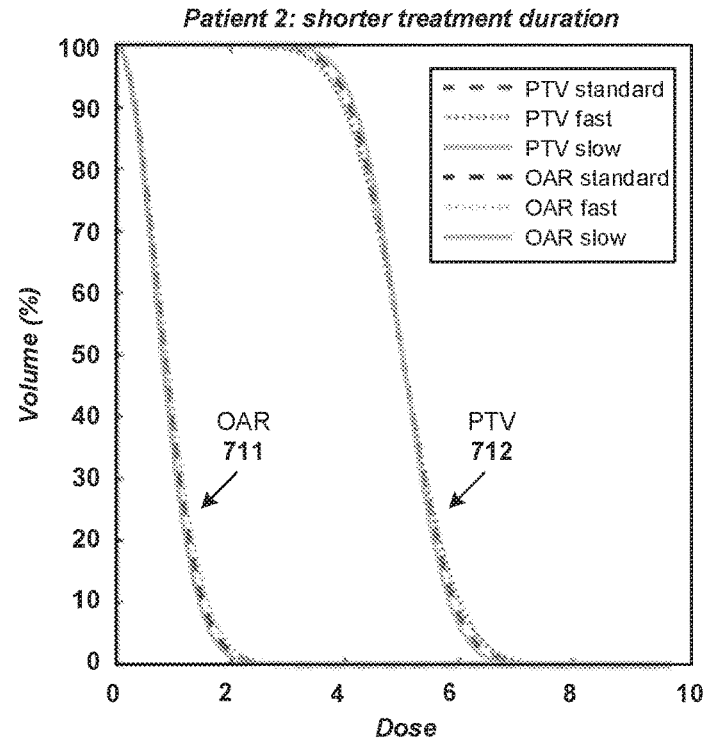
FIG. 7B is a graph illustrating example DVH curves associated with a second patient case.

Some example patient cases are shown in FIGS. 7A-B. Here, FIG. 7A is a graph illustrating example DVH curves 700 associated with a first patient case and FIG. 7B is a graph illustrating example DVH curves 710 associated with a second patient case. The two patient cases are different in how sensitive the achieved treatment plan quality is to the delivery speed. Different treatment delivery speeds are labelled as "standard," "fast" and "slow." "Fast" indicates shorter treatment duration, "slow" indicates longer treatment duration and "standard" somewhere in between. Treatment plan quality may be associated with "OAR" volume (see 701/711) and target volume "PTV" (see 702/712).

For the first patient case in FIG. 7A, treatment plan quality may depend critically on the length of treatment duration. In this case, better treatment plan quality may be achieved using longer treatment duration. For the second patient case in FIG. 7B, however, there is an opportunity to improve treatment delivery efficiency according to examples of the present disclosure. Here, treatment plan quality is observed to be quite similar for different treatment durations. Using the examples in FIGS. 4-6, a treatment plan with clinically acceptable quality and relatively shorter treatment duration may be selected during Pareto surface navigation.

According to examples of the present disclosure, treatment delivery efficiency may be introduced as an added dimension in MCO for radiotherapy treatment planning. This way, a set of anchor plans (that are considered to span an interesting portion of the Pareto surface) may be enlarged by adding solutions with different treatment durations. In general, the treatment duration is difficult to formulate mathematically. Using examples of the present disclosure, any input or feedback from planners and clinicians may be considered during radiotherapy treatment planning to reject or accept a treatment plan according to blocks 460-490 in FIG. 4.

In practice, dose distributions obtained at different durations may be interpolated to obtain a dose distribution at any treatment duration. From dose distribution, DVH curves may be calculated and used to evaluate the treatment plan quality interactively. Non-trivial interpolation between optimized treatment plans may be performed on the dose distributions when PLAN_k is updated at step 480. Mathematically, the interpolated dose distribution is not necessarily obtainable between data points, but the error in the interpolated and actual dose distribution is likely to be small. The interpolation error may also be controlled by changing the number of treatment plan variants 540, such as by using different speed limits for VMAT or fluence smoothing parameters for IMRT. A denser collection of treatment plans 540 generally reduces the interpolation error. In order to reduce the difference between real treatment duration and interpolated treatment duration, treatment plan variants 540 may be generated by continuing optimization from an initial navigation plan instead of starting optimization from the beginning.

Multiple Pareto Surfaces

Depending on the desired implementation, any additional and/or alternative steps may be performed during Pareto surface navigation at blocks 460-490. One example involves the generation of multiple Pareto surfaces. In practice, a Pareto surface is generally drawn by varying the weights of different objective functions. In this case, optimization may be performed multiple times with different set of weights and each optimization result is a single point on the Pareto-surface. To generate multiple Pareto surfaces, objective function(s) may be altered using any suitable approach.

Figure 8:
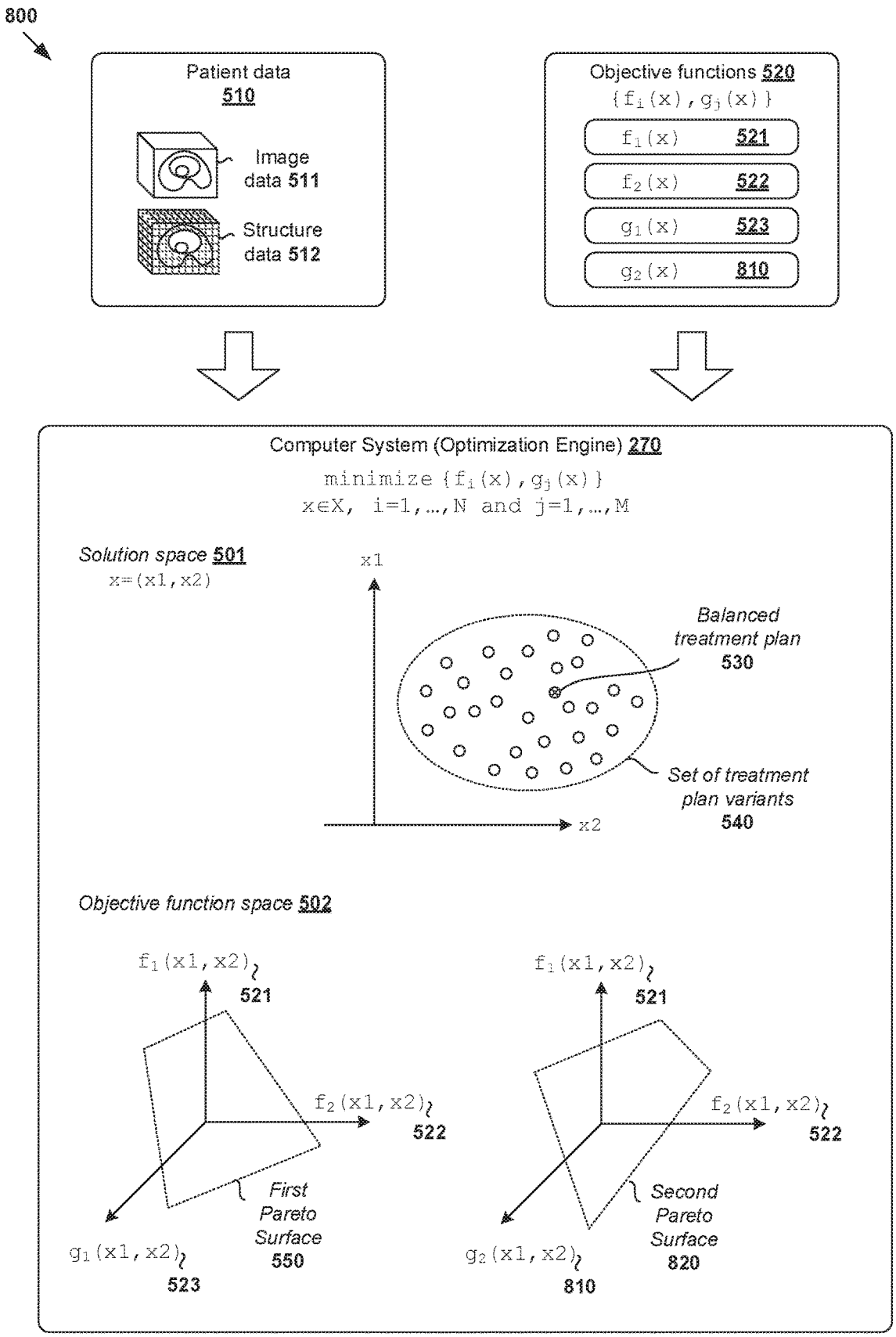
FIG. 8 is a schematic diagram illustrating example generation of multiple Pareto surfaces for radiotherapy treatment planning based on treatment delivery efficiency.

(i) A first approach is shown in FIG. 8, which is a schematic diagram illustrating example generation 800 of multiple Pareto surfaces for radiotherapy treatment planning based on treatment delivery efficiency. Similar to FIG. 5, a first Pareto surface (see 550) may be generated based on $f_1(x)$, $f_2(x)$ and $g_1(x)$ that represents a first treatment duration preference; see 521-523. Additionally, a second Pareto surface (see 820) may be generated based on $f_1(x)$, $f_2(x)$ and $g_2(x)$ that represents a different treatment duration preference; see 521-522, 810. The latter (i.e., $g_2(x)$) may allow for treatment plans with longer treatment duration but dosimetrically better treatment may lead the optimizer to find different trade-offs between plan quality and treatment duration. In this case, the same objective function weight may be assigned to both $g_1(x)$ and $g_2(x)$.

(ii) A second approach for generating multiple Pareto surfaces may involve assigning different weights to the same objective function, the weight being considered as a discrete variable rather than continuous. For example, first Pareto surface 550 may be generated based on a first weight (w1) assigned to $g_j(x)$. Second Pareto surface 820 may be generated based on a second weight (w2) assigned to the same $g_1(x)$.

(iii) A third approach for generating multiple Pareto surfaces may involve using the same objective functions but different constraints (presenting different treatment time preferences). For example, first Pareto surface 550 may be created using 2-field VMAT field geometry and second Pareto surface 820 using 3-field VMAT field geometry. In practice, three fields generally lead to better treatment plan quality but longer treatment duration.

Any suitable approach may be used for navigating a discontinuous Pareto set (see example in FIG. 8). One possible implementation would involve performing the navigation on first Pareto surface 550, but presenting (at every iteration of the Pareto surface navigation) also a selected plan lying in the second Pareto surface 820. The plan in second Pareto surface 820 may be selected as the one being closest to the currently selected plan in first Pareto surface 550. This way, optimization of treatment delivery efficiency may be performed based on a larger set of treatment plan variants.

Depending on the desired implementation, navigation of multiple Pareto surfaces may be performed at the same time until a treatment plan of desired dosimetric quality and efficiency is identified. Alternatively, one of the Pareto surfaces may be navigated, while the other Pareto surface would follow a weighting resolved from the first Pareto surface. In this case, the navigation process may take into account the effect of a discrete parameter. Example discrete parameters may include MLC technique (e.g., VMAT or IMRT), use of optimization option (e.g., ASCO), choice of primary fluence mode (e.g. standard mode, flattening filter free (FFF) mode), etc.

Example Treatment Plan

Figure 9:
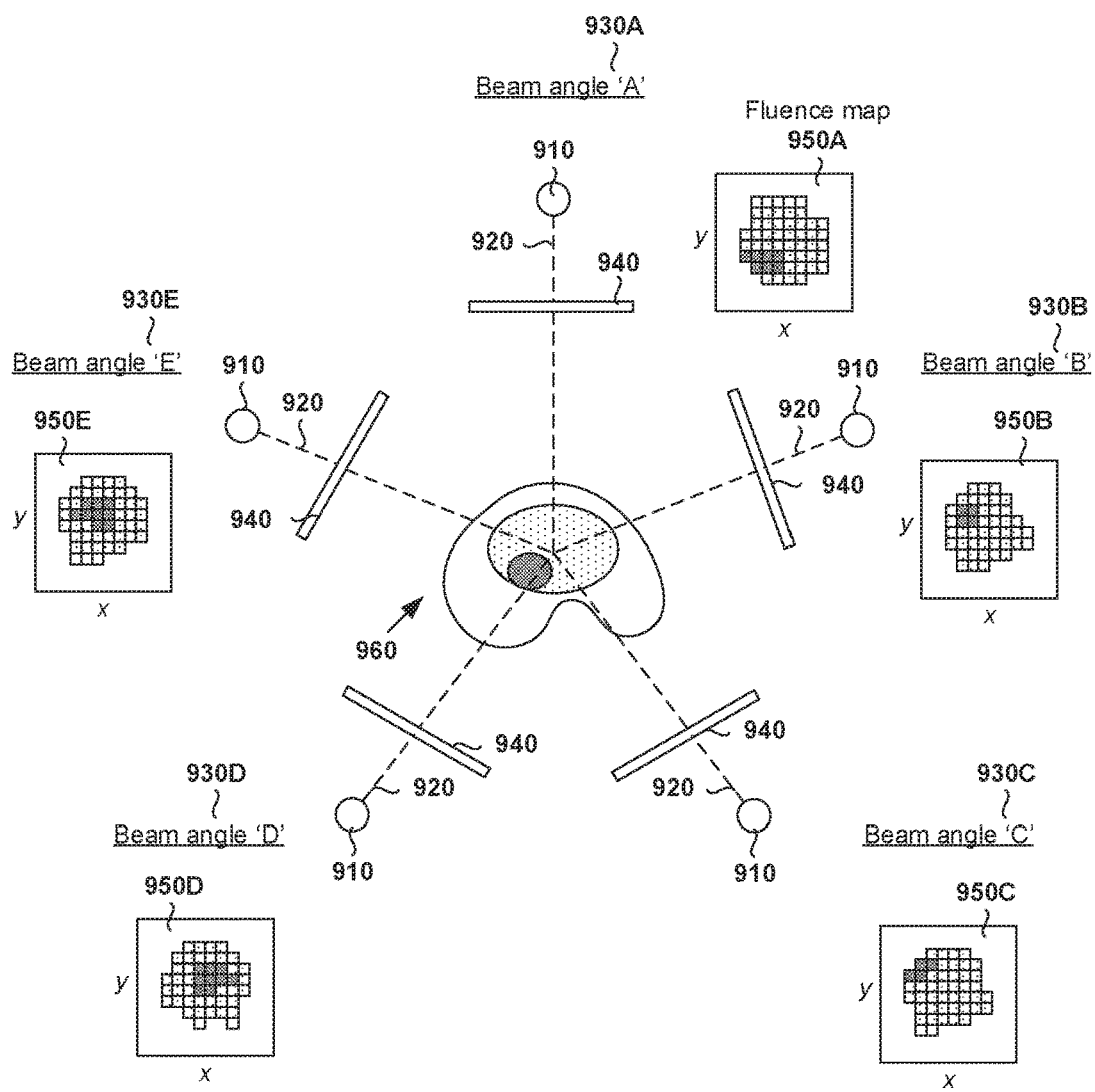
FIG. 9 is a schematic diagram of an example treatment plan for radiotherapy treatment delivery based on treatment delivery efficiency.

FIG. 9 is a schematic diagram of an example treatment plan generated or improved based on examples of the present disclosure. Treatment plan 156 (i.e., output of computer system 290) may be delivered using any suitable treatment delivery system that includes radiation source 910 to project radiation beam 920 onto treatment volume 960 representing the patient's anatomy at various beam angles 930. Although not shown in FIG. 9 for simplicity, radiation source 910 may include a linear accelerator to accelerate radiation beam 920 and a collimator (e.g., MLC) to modify or modulate radiation beam 920. In another example, radiation beam 920 may be modulated by scanning it across a target patient in a specific pattern with various energies and dwell times (e.g., as in proton therapy). A controller (e.g., computer system) may be used to control the operation of radiation source 920 according to treatment plan 156.

During treatment delivery, radiation source 910 may be rotatable using a gantry around a patient, or the patient may be rotated (as in some proton radiotherapy solutions) to emit radiation beam 920 at various beam orientations or angles relative to the patient. For example, five equally spaced beam angles 930A-E (also labeled "A," "B," "C," "D" and "E") may be selected. In practice, any suitable number of beam and/or table or chair angles 930 (e.g., five, seven) may be selected. At each beam angle, radiation beam 920 is associated with fluence plane 940 (also known as an intersection plane) situated outside the patient envelope along a beam axis extending from radiation source 910 to treatment volume 960. As shown in FIG. 9, fluence plane 940 is generally at a known distance from the isocenter.

In addition to beam angles 930A-E, fluence parameters of radiation beam 920 are required for treatment delivery. The term "fluence parameters" may refer generally to characteristics of radiation beam 920, such as its intensity profile as represented using fluence maps (e.g., 950A-E for corresponding beam angles 930A-E). Each fluence map (e.g., 950A) represents the intensity of radiation beam 920 at each point on fluence plane 940 at a particular beam angle (e.g., 930A). Treatment delivery may then be performed according to fluence maps 950A-E, such as using IMRT, etc. The radiation dose deposited according to fluence maps 950A-E should, as much as possible, correspond to the treatment plan generated according to examples of the present disclosure.

Computer System

Figure 10:
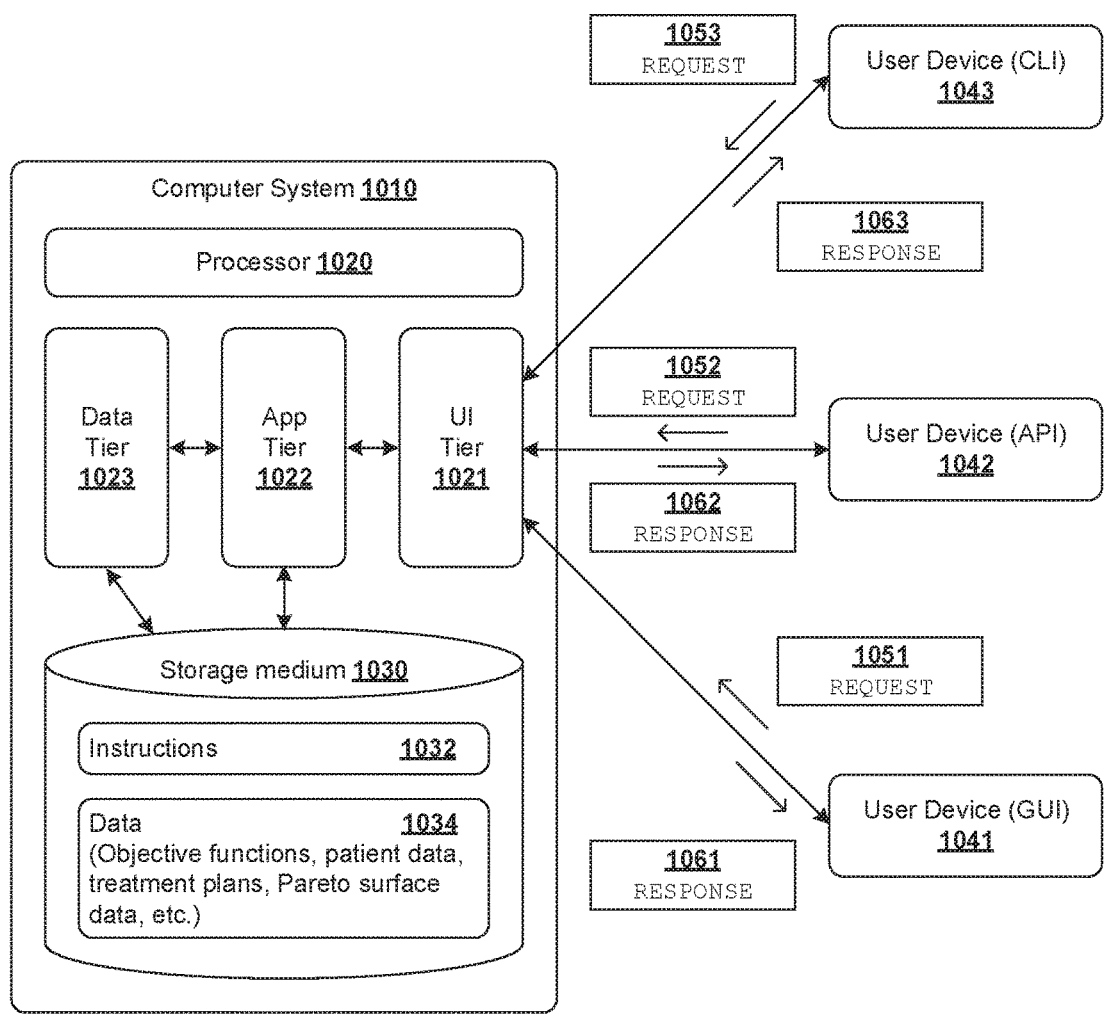
FIG. 10 is a schematic diagram of an example computer system to perform example radiotherapy treatment planning based on treatment delivery efficiency.

Examples of the present disclosure may be deployed in any suitable manner, such as a standalone system or a web-based system (e.g., planning-as-a-service (PaaS) system). In the following, an example computer system (also known as a "planning system") will be described using FIG. 10, which is a schematic diagram illustrating example network environment 1000 in which radiotherapy treatment planning may be implemented. Depending on the desired implementation, network environment 1000 may include additional and/or alternative components than that shown in FIG. 10. Examples of the present disclosure may be implemented by hardware, software or firmware or a combination thereof.

Computer system 1010 (related to 270 in FIG. 2) includes processor 1020 that is configured to perform processes described herein with reference to FIG. 1 to FIG. 7. Computer-readable storage medium 1030 may store computer-readable instructions 1032 which, in response to execution by processor 1020, cause processor 1020 to perform various processes described herein. Computer-readable storage medium 1030 may further store any suitable data 1034, such as data relating to dosimetric objective function(s), non-dosimetric objective function(s), patient data, treatment plans, etc. In the example in FIG. 10, computer system 1010 may be accessible by multiple user devices 1041-1043 via any suitable physical network (e.g., local area network, wide area network). User devices 1041-1043 may be operated by various users located at any suitable clinical site(s).

Computer system 1010 may be implemented using a multi-tier architecture that includes web-based user interface (UI) tier 1021, application tier 1022, and data tier 1023. UI tier 1021 may be configured to provide any suitable interface(s) to interact with user devices 1041-1043, such as graphical user interface (GUI), command-line interface (CLI), application programming interface (API) calls, any combination thereof, etc. Application tier 1022 may be configured to implement examples of the present disclosure. Data tier 1023 may be configured to facilitate data access to and from storage medium 1030. By interacting with UI tier 1021, user devices 1041-1043 may generate and send respective requests 1051-1053 for processing by computer system 1010. In response, computer system 1010 may perform examples of the present disclosure generate and send service responses 1061-1063 to respective user devices 1041-1043.

Depending on the desired implementation, computer system 1010 may be deployed in a cloud computing environment, in which case multiple virtualized computing instances (e.g., virtual machines, containers) may be configured to implement various functionalities of tiers 1021-1023. The cloud computing environment may be supported by on premise cloud infrastructure, public cloud infrastructure, or a combination of both. Computer system 1010 may be deployed in any suitable manner, including a service-type deployment in an on-premise cloud infrastructure, public cloud infrastructure, a combination thereof, etc. Computer system 1010 may represent a computation cluster that includes multiple computer systems among which various functionalities are distributed. Computer system 1010 may include any alternative and/or additional component(s) not shown in FIG. 10, such as graphics processing unit (GPU), message queues for communication, blob storage or databases, load balancer(s), specialized circuits, etc.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to perform radiotherapy treatment planning based on treatment delivery efficiency, wherein the method comprises:
    configuring at least one dosimetric planning objective for a subject requiring radiotherapy treatment;
    configuring at least one non-dosimetric planning objective based on a parameter for operation of a radiotherapy treatment delivery system, wherein the parameter affects efficiency of treatment delivery by the radiotherapy treatment delivery system to the subject;
    generating a set of multiple treatment plan variants based on the at least one dosimetric planning objective and the at least one non-dosimetric planning objective;
    identifying, from the set of multiple treatment plan variants, a first treatment plan associated with a first tradeoff among the at least one dosimetric planning objective and the at least one non-dosimetric planning objective; and
    identifying, from the set of multiple treatment plan variants, a second treatment plan associated with a second tradeoff that varies from the first tradeoff, wherein the second treatment plan is associated with improved efficiency of treatment delivery compared to the first treatment plan.

2. The method of claim 1, wherein configuring the at least one non-dosimetric planning objective based on the parameter comprises:
    configuring the at least one non-dosimetric objective based on one or more of the following parameters: treatment delivery duration, monitor unit, fluence smoothing level, adjacent leaf synchronization level, dose rate modulation level, leaf modulation level, primary fluence mode, number of treatment fields, number of isocenter positions, allowed range for a machine axis, maximum machine axis speed and type of multi-leaf collimator (MLC) technique.

3. The method of claim 1, wherein generating the set of multiple treatment plan variants comprises:
    generating the set of multiple treatment plan variants that are associated with respective levels of efficiency in the form of treatment delivery durations.

4. The method of claim 3, wherein generating the set of multiple treatment plan variants comprises:
    generating, for treatment delivery based on volumetric modulated arc therapy (VMAT), the set of multiple treatment plan variants by scaling at least one of the following: dose speed limit, gantry speed limit and collimator leaf speed limit.

5. The method of claim 3, wherein generating the set of multiple treatment plan variants comprises:
    generating, for treatment delivery based on intensity modulation radiotherapy treatment (IMRT), the set of multiple treatment plan variants by varying an IMRT fluence smoothing parameter.

6. The method of claim 1, wherein generating the set of multiple treatment plan variants comprises:
    generating a balanced treatment plan based on an equal tradeoff among the at least one dosimetric planning objective and the at least one non-dosimetric planning objective; and
    generating the set of multiple treatment plan variants based on the balanced treatment plan.

7. The method of claim 1, wherein identifying the second treatment plan comprises:
    constructing a Pareto surface based on the set of multiple treatment plan variants, being Pareto-optimal treatment plans; and
    starting from a point representing the first treatment plan on the Pareto surface, navigating the Pareto surface to identify the second treatment plan associated with the improved efficiency of treatment delivery.

8. A non-transitory computer-readable storage medium that includes a set of instructions which, in response to execution by a processor of a computer system, cause the processor to perform a method of radiotherapy treatment planning based on treatment delivery efficiency, wherein the method comprises:
    configuring at least one dosimetric planning objective for a subject requiring radiotherapy treatment;
    configuring at least one non-dosimetric planning objective based on a parameter for operation of a radiotherapy treatment delivery system, wherein the parameter affects efficiency of treatment delivery by the radiotherapy treatment delivery system to the subject;
    generating a set of multiple treatment plan variants based on the at least one dosimetric planning objective and the at least one non-dosimetric planning objective;
    identifying, from the set of multiple treatment plan variants, a first treatment plan associated with a first tradeoff among the at least one dosimetric planning objective and the at least one non-dosimetric planning objective; and
    identifying, from the set of multiple treatment plan variants, a second treatment plan associated with a second tradeoff that varies from the first tradeoff, wherein the second treatment plan is associated with improved efficiency of treatment delivery compared to the first treatment plan.

9. The non-transitory computer-readable storage medium of claim 8, wherein configuring the at least one non-dosimetric planning objective based on the parameter comprises:

configuring the at least one non-dosimetric objective based on one or more of the following parameters: treatment delivery duration, monitor unit, fluence smoothing level, adjacent leaf synchronization level, dose rate modulation level, leaf modulation level, primary fluence mode, number of treatment fields, number of isocenter positions, allowed range for a machine axis, maximum machine axis speed and type of multi-leaf collimator (MLC) technique.

10. The non-transitory computer-readable storage medium of claim 8, wherein generating the set of multiple treatment plan variants comprises:

generating the set of multiple treatment plan variants that are associated with respective levels of efficiency in the form of treatment delivery durations.

11. The non-transitory computer-readable storage medium of claim 10, wherein generating the set of multiple treatment plan variants comprises:

generating, for treatment delivery based on volumetric modulated arc therapy (VMAT), the set of multiple treatment plan variants by scaling at least one of the following: dose speed limit, gantry speed limit and collimator leaf speed limit.

12. The non-transitory computer-readable storage medium of claim 10, wherein generating the set of multiple treatment plan variants comprises:

generating, for treatment delivery based on intensity modulation radiotherapy treatment (IMRT), the set of multiple treatment plan variants by varying an IMRT fluence smoothing parameter.

13. The non-transitory computer-readable storage medium of claim 8, wherein generating the set of multiple treatment plan variants comprises:

generating a balanced treatment plan based on an equal tradeoff among the at least one dosimetric planning objective and the at least one non-dosimetric planning objective; and
generating the set of multiple treatment plan variants based on the balanced treatment plan.

14. The non-transitory computer-readable storage medium of claim 8, wherein identifying the second treatment plan comprises:

constructing a Pareto surface based on the set of multiple treatment plan variants, being Pareto-optimal treatment plans; and
starting from a point representing the first treatment plan on the Pareto surface, navigating the Pareto surface to identify the second treatment plan associated with the improved efficiency of treatment delivery.

15. A computer system, comprising a processor and a non-transitory computer-readable medium having stored thereon instructions that, when executed by the processor, cause the processor to:

configure at least one dosimetric planning objective for a subject requiring radiotherapy treatment;
configure at least one non-dosimetric planning objective based on a parameter for operation of a radiotherapy treatment delivery system, wherein the parameter affects efficiency of treatment delivery by the radiotherapy treatment delivery system to the subject;
generate a set of multiple treatment plan variants based on the at least one dosimetric planning objective and the at least one non-dosimetric planning objective;
identify, from the set of multiple treatment plan variants, a first treatment plan associated with a first tradeoff among the at least one dosimetric planning objective and the at least one non-dosimetric planning objective; and
identify, from the set of multiple treatment plan variants, a second treatment plan associated with a second tradeoff that varies from the first tradeoff, wherein the second treatment plan is associated with improved efficiency of treatment delivery compared to the first treatment plan.

16. The computer system of claim 15, wherein the instructions for configuring the at least one non-dosimetric planning objective based on the parameter cause the processor to:

configure the at least one non-dosimetric objective based on one or more of the following parameters: treatment delivery duration, monitor unit, fluence smoothing level, adjacent leaf synchronization level, dose rate modulation level, leaf modulation level, primary fluence mode, number of treatment fields, number of isocenter positions, allowed range for a machine axis, maximum machine axis speed and type of multi-leaf collimator (MLC) technique.

17. The computer system of claim 15, wherein the instructions for generating the set of multiple treatment plan variants cause the processor to:

generate the set of multiple treatment plan variants that are associated with respective levels of efficiency in the form of treatment delivery durations.

18. The computer system of claim 15, wherein the instructions for generating the set of multiple treatment plan variants cause the processor to:

generate, for treatment delivery based on volumetric modulated arc therapy (VMAT), the set of multiple treatment plan variants by scaling at least one of the following: dose speed limit, gantry speed limit and collimator leaf speed limit.

19. The computer system of claim 18, wherein the instructions for generating the set of multiple treatment plan variants cause the processor to:

generate, for treatment delivery based on intensity modulation radiotherapy treatment (IMRT), the set of multiple treatment plan variants by varying an IMRT fluence smoothing parameter.

20. The computer system of claim 15, wherein the instructions for generating the set of multiple treatment plan variants cause the processor to:

generate a balanced treatment plan based on an equal tradeoff among the at least one dosimetric planning objective and the at least one non-dosimetric planning objective; and
generating the set of multiple treatment plan variants based on the balanced treatment plan.

21. The computer system of claim 15, wherein the instructions for identifying the second treatment plan cause the processor to:

construct a Pareto surface based on the set of multiple treatment plan variants, being Pareto-optimal treatment plans; and
starting from a point representing the first treatment plan on the Pareto surface, navigate the Pareto surface to identify the second treatment plan associated with the improved efficiency of treatment delivery.

* * * * *